(12) United States Patent
Tempesta et al.

(10) Patent No.: US 12,280,067 B2
(45) Date of Patent: *Apr. 22, 2025

(54) FORMULATIONS OF CREATINE AND CYCLODEXTRIN EXHIBITING IMPROVED BIOAVAILABILITY

(71) Applicants: Michael S Tempesta, El Granada, CA (US); F. Joseph Daugherty, Omaha, NE (US)

(72) Inventors: Michael S Tempesta, El Granada, CA (US); F. Joseph Daugherty, Omaha, NE (US)

(73) Assignee: Phenolics, LLC, Omaha, NE (US)

( * ) Notice: Subject to any disclaimer, the term of this patent is extended or adjusted under 35 U.S.C. 154(b) by 263 days.

This patent is subject to a terminal disclaimer.

(21) Appl. No.: 16/392,475

(22) Filed: Apr. 23, 2019

(65) Prior Publication Data

US 2022/0211729 A1 Jul. 7, 2022

(51) Int. Cl.

| | | |
|---|---|---|
| *A61K 31/664* | (2006.01) | |
| *A61K 9/00* | (2006.01) | |
| *A61K 9/50* | (2006.01) | |
| *A61K 31/205* | (2006.01) | |
| *A61K 47/10* | (2017.01) | |
| *A61K 47/40* | (2006.01) | |

(52) U.S. Cl.
CPC .......... *A61K 31/664* (2013.01); *A61K 9/0053* (2013.01); *A61K 9/5026* (2013.01); *A61K 31/205* (2013.01); *A61K 47/10* (2013.01); *A61K 47/40* (2013.01)

(58) Field of Classification Search
CPC .. A61K 31/664; A61K 9/0053; A61K 9/5026; A61K 31/205; A61K 47/10; A61K 47/40; A61K 9/0095; A61K 9/1652
See application file for complete search history.

(56) References Cited

U.S. PATENT DOCUMENTS

| | | | | |
|---|---|---|---|---|
| 3,036,087 | A * | 5/1962 | Anatol | C07F 9/22 562/560 |
| 2006/0062849 | A1 | 3/2006 | Byrd | |
| 2008/0306159 | A1* | 12/2008 | Daugherty | A61K 9/286 514/565 |
| 2010/0055178 | A1* | 3/2010 | Vilallobos | A61K 31/197 424/490 |

(Continued)

OTHER PUBLICATIONS

Fenvesi (Cyclodextrins in Food Technology and Human Nutrition: Benefits and Limitations, Critical Reviews in Food Science and Nutrition, 56:1981-2004). (Year: 2016).*

(Continued)

*Primary Examiner* — Benjamin J Packard
*Assistant Examiner* — Joshua A Atkinson
(74) *Attorney, Agent, or Firm* — McGrath North Mullin & Kratz, PC LLO; Jeanne J. Kelley

(57) ABSTRACT

Formulations of creatine, preferably phosphocreatine and most preferably disodium phosphocreatine, combined with cyclodextrin exhibit improved uptake across digestive mucosa, including intestinal, esophageal, and stomach mucosa. In particular, the formulations of the present invention are designed for protection of the cyclodextrin as it comes in contact with gastric juices so as to allow thereafter for unexpectedly improved site-specific intestinal release.

20 Claims, 3 Drawing Sheets

(56) References Cited

U.S. PATENT DOCUMENTS

2017/0173100 A1* 6/2017 Antony ............... A61K 36/82
2022/0211729 A1   7/2022 Tempesta

OTHER PUBLICATIONS

Dash, A. K., Mo, Y., & Pyne, A. (2002). Solid-state properties of creatine monohydrate. Journal of Pharmaceutical Sciences, 91(3), 708-718.
Zou LL, Li QS, Han GZ, Lü L, Xi H, Li JH. Pharmacokinetics and metabolic disposition of exogenous phosphocreatine in rats. Yao Xue Xue Bao. Jan. 2011;46(1):75-80. Chinese. PMID: 21465812.
Peeters, Brian M.; Lantz, Christopher D.; Mayhew, Jerry L.. Effect of Oral Creatine Monohydrate and Creatine Phosphate Supplementation on Maximal Strength Indices, Body Composition, and Blood Pressure. Journal of Strength and Conditioning Research 13(1):p. 3-9, Feb. 1999.
Tricarico D, Casini G, Conte Camerino D. Effects of high energy phosphates and L-arginine on the electrical parameters of ischemic-reperfused rat skeletal muscle fibers. Eur J Pharmacol. Dec. 4, 1995;287(1): 17-25.
Del Valle, E.M.M. (2004) Cyclodextrins and Their Uses: A Review. Process Biochemistry, 39, 1033-1046.
Dash AK, Miller DW, Huai-Yan H, Camazzo J, Stout JR. Evaluation of creatine transport using Caco-2 monolayers as an in vitro model for intestinal absorption. J Pharm Sci. Oct. 2001;90(10):1593-8.

* cited by examiner

FORMULATIONS OF CREATINE AND CYCLODEXTRIN EXHIBITING IMPROVED BIOAVAILABILITY

PRIORITY

This application claims priority of U.S. Provisional Application No. 62/674,086 filed May 21, 2018, which is incorporated herein in its entirety by this reference.

FIELD OF THE INVENTION

The present invention relates to formulations of creatine and cyclodextrin having improved bioavailability. More particularly, the present invention relates to formulations of phosphocreatine (especially disodium phosphocreatine) combined with cyclodextrin exhibiting improved uptake across digestive mucosa, including intestinal, esophageal, and stomach mucosa. In particular, the formulations of the present invention are designed for protection of the cyclodextrin as it comes in contact with gastric juices and thereafter site-specific intestinal release.

BACKGROUND OF THE INVENTION

It is known that dietary ingestion of creatine monohydrate is preferentially taken up by skeletal muscle. Indeed, creatine is used heavily as a dietary supplement for performance enhancement by athletes. This is because the creatine, once present muscle tissue where it is stored as creatine phosphate, reacts with adenosine diphosphate (ADP) to restore adenosine triphosphate (ATP) levels and provide energy needed for muscle activity. By ingesting creatine, athletes are able to load their muscle tissue with higher levels of creatine phosphate and are able to better sustain muscle activity.

Although many forms of creatine are stable ex vivo, including the creatine monohydrate and numerous esters, creatine and creatine monohydrate are known to be typically unstable in vivo, i.e., in the acidic environment that exists in the stomach, and the basic conditions of the lower gastrointestinal tract. So, for example, it is known that creatine monohydrate, which is a commonly ingested form of creatine, can rapidly break down in the stomach to form creatinine. Furthermore, because creatine monohydrate is not easily fully solubilized in cold or room temperature water, it is often dissolved in fruit juices and other acidic liquids, which also promote degradation of creatine to creatinine and excretion. For these reasons, other forms of creatine, particularly creatine ethyl esters, have been the focus of product development. However, such compounds also suffer from solubility and degradation problems. Properties of creatine monohydrate ($C_4H_{11}N_3O_3$) are described in more detail in A. K. Dash, et al., "Solid State Properties of Creatine Monohydrate", Journ. of Pharm. Sciences, Vol. 91, No. 3, March 2002, pp. 708-717.

In an effort to create a stable form of creatine in which the creatine would be better protected from degradation while present in the stomach and intestines, various oral creatine formulations have been described which are characterized as controlled release delivery agents. For example, U.S. Patent Application Publication No. 2006/0062849 A1 to Byrd, described oral formulations of creatine derivatives which preferably include creatine ethyl esters, a phosphate such as dicalcium phosphate, a biodegradable polymer such as polyvinyl pyrrolidine and a starch. See Byrd Abstract. The formulation is described as containing flowable particles having a sieve size of about 20-60 coated with shellac. Id. Byrd describes certain "quick release" formulations of its disclosed creatine derivatives as having improved bioavailability, as distinguished from "Controlled Release Technology". See Byrd [0086] et seq. Controlled release technologies listed in Byrd are described as including known techniques by many names, including "continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release." Id at [0087]. Enteric coatings are described as one preferable type of oral controlled release structure, Id at [0100], with preferable coating agents including "hydroxypropylmethylcellulose phthalate, methacrylic acid-methacrylic acid ester copolymer, polyvinyl acetate-phthalate and cellulose acetate phthalate." id at [0101].

Even if a particular form of creatine is protected from degradation prior to desired point of uptake in the digestive tract, once the creatine arrives at the area in the digestive where uptake is desired, transport across the particular mucosal cells is not fully understood and often suboptimal. To more easily test cell transport using a model which meaningfully approximates in vivo digestive tract absorption, researchers now utilize the Caco-2 cell line, a continuous cell of heterogeneous epithelial adenocarcinoma cells developed by the Sloan-Kettering Institute for Cancer Research, which resembles enterocytes lining the small intestine. Utilization of the Caco-2 cell line to measure creatine transport was described by researchers at the University of Nebraska Medical Center in the following publication: A. K. Dash, et al., "Evaluation of Creatine Transport Using Caco-2 Monolayers as an in Vitro Model for Intestinal Absorption", Journ. of Pharm. Sciences, Vol. 90, No. 10, Oct. 10, 2001, pp. 1593-98. The article describes how the researchers examined creatine transport using confluent monolayers Caco-2 for their permeability studies. It concluded that permeability of creatine via Caco-2 monolayers was quite low and bidirectional in nature. It was also found that utilization of an effervescent formulation of creatine did not enhance membrane transport properties. So, although superior technique of enhanced uptake of creatine did not result from this research project, a viable in vivo method of testing creatine transport across mucosal cells was described.

Uptake of exogenous phosphocreatine has been studied. For example, in Zou, L., et al., "*Pharmacokinetics and metabolic disposition of exogenous phosphocreatine in rats*", a study of the pharmacokinetics and metabolic disposition of exogenous phosphocreatine in rats was conducted in which phosphocreatine was injected in rats intravenously and phosphocreatine, its metabolite creatine, and ATP in blood were subsequently measured by means of ion-pair HPLC-UV assay. The study concluded that the phosphocreatine administration resulted in significant elevation of ATP levels in red blood cells, no phosphocreatine was detected in the red blood cells within 65-95 minutes, significant creatine was detected, and the phosphocreatine was bio-transformed and eliminated in the body very rapidly.

The term "phosphocreatine" commonly refers to N-Methyl-N-(phosphono-carbamimidoyl)glycine having a chemical formulation of $C_4H_{10}N_3O_5P$, a molar mass of 211.11 g/mol and a CAS Registry No. 67-07-2. It is also referred to in abbreviated form as PCr.

A study by Brian Peeters, et al., entitled "*Effect of Oral Creatine Monohydrate and Creatine Phosphate Supplementation on Maximal Strength Indices, Body Composition, and Blood Pressure*", Journ. of Strength and Conditioning Research, 1999, 13(1), 3-9, compares the effect of creatine monohydrate, creatine, and creatine phosphate supplementation on strength, body composition, and blood pressure over a 6-week period. The study concludes that oral creatine phosphate supplementation may be as effective as creatine monohydrate in achieving lean body mass, desired body weight, and improved strength (as reflected in bench press testing).

In yet another study, this one by D. Tricarico, et al. entitled "*Effects of high energy phosphates and L-arginine on the electrical parameters of ischemic-reperfused rat skeletal muscle fibers*", European Journ. of Pharm., 287 (1995) 17-25, certain muscles in rats were measured in vitro by a computerized two-intracellular microelectrode technique, before and after in vivo pretreatment with phosphocreatine disodium salt tetrahydrate, phosphocreatine di-L-arginine salt, and L-arginine hydrochloride. It was reported that phosphocreatine salts prevented the increase of muscle ion conductance by preloading the muscle fibers with ATP.

Nonetheless, it is believed that a significantly improved formulation of creatine is needed to substantially improve bioavailability and uptake without including minimally helpful and unnecessary constituents, in order to advance the pharmacokinetics and pharmacodynamics aspects of the formulations. Such technical improvements should also allow a set of new uses to possibly address more effectively disorders such as cachexia and Sarcopenia in addition to traditional muscle building and maintenance applications to which creatine and/or leucine supplementation have been historically directed.

SUMMARY OF THE INVENTION

In a preferred formulation of the supplement to be manufactured by the method of the present invention, creatine and cyclodextrin are co-granulated. The form of the creatine to be co-granulated is preferably selected from the group consisting of phosphocreatine, creatine HCl and creatine monohydrate. A most preferred formulation includes disodium phosphocreatine, as such a formulation provides a substantial and sufficient quantity of sodium to optimize transport and absorption, and therefore bioavailability of the creatine from the intestines. Otherwise a sufficient amount of sodium must be included in the product to be coated with the methacrylate copolymers according to the methods of the present invention. A sufficient amount of sodium most preferably constitutes from about 1 to about 3 parts sodium (molar equivalent) for each part creatine (molar equivalent). The use of disodium phosphocreatine as the primary sodium and creatine sources in the method and formulations of the present invention results is most preferred, most preferably in a molecular ratio of sodium to creatine of 2:1.

As used herein, disodium phosphocreatine is distinguished from phosphocreatine in it is a salt with a different CAS Registry No. 922-32-7 a different molecular formula ($C_4H_8N_3Na_2O_5P$) and a molar mass of 255.08 g/mol (anhydrous). It is also may be referred to as creatine phosphate disodium salt. Sodium creatine phosphate dibasic tetrahydrate is a related product having a molecular weight of 327.14, a CAS Registry No. of 71519-72-7. While the former product is an anhydrous form, and the latter product is a hydrated form, the tetrahydrate is sometimes also referred to as disodium phosphocreatine.

α-, β- and/or γ-cyclodextrins and other excipients are used in the methods and compositions of the present invention also containing creatine, especially phosphocreatines, and in particular disodium phosphocreatine with unexpectedly effective uptake. Cyclodextrins are cyclic oligosaccharides having glucopyranose units linked by α-(1-4) bonds. α-, β- and γ-cyclodextrins are composed of 6, 7 and 8 α-(1-4)-linked glycosyl units, respectively. See, E. M. M. Del Valle, *Process Biochemistry*, vol. 39, Issue 9, (2004) pg. 1033-1076. The outer diameters cavity diameters and cavity volume are different for α-, β- and γ-cyclodextrins. Id. Furthermore, crystal packing and channel and cage structures depending on the guest compound. Id. Cyclodextrins form solid inclusion complexes in which a guest molecule is held within the cavity of the cyclodextrin host. Id. While the microenvironment of the lipophilic cyclodextrin cavity allows for complex formation by the displacement of water from the cavity, the nature and shape of the guest molecule, as well as the particular mixture of α-, β- and γ-cyclodextrins being mixed with the guest molecules, means that the resulting reactivity and disassociation of the cyclodextrins from the guest molecules cannot necessarily be accurately predicted. In the experiments described herein, γ-cyclodextrins are primarily employed. However, substantially pure α-, and β-cyclodextrins also may be utilized, and mixtures of two or three of the α-, β- and γ-cyclodextrins are also preferred.

More particularly, the inventors of the present invention discovered that when disodium phosphocreatine is included in the methods and compositions of the present invention and an α-cyclodextrin is also included, the particular size of the hydrophobic and lipophilic interior optimally accommodates the non-polar moiety of the creatine, and allows the more polar moiety(ies) of the disodium phosphocreatine to extend outwardly beyond the interior of the cyclodextrin structure. It is believed that during digestion, the cyclodextrin moiety protects the creatine as it passes through the stomach and comes in contact with the acidic contents of the stomach, but allows for subsequent bonding and separation of the creatine from the cyclodextrin as the product passes through the intestines where the cyclodextrin is transported across cellular membranes in a controlled manner.

In one aspect of the manufacture of the present invention, supplements are produced by wet or dry co-granulation of active materials with excipients: The co-granulated ingredients are then coated with controlled release methacrylate copolymers, most preferably using spray drying, fluidized bed techniques. Preferably, the active ingredients are co-granulated to an average size of 150 to 840μ (microns) in size, more preferably to an average size of 250-500μ, and most preferably to an average size of 350-450μ. The size and co-granulation time are sized and selected to result in particles within a specific range and to allow for raw material uniformity. US Mesh screens of 20-100 are preferably used to ensure that the particles are suitable for subsequent tableting or used as powders, as desired. The preferred particle size is selected with an eye to interlocking particular active ingredient(s) with other constituents, as is further described herein. In the preferred embodiments, co-granulated constituents are combining these materials with a coating agent by utilizing a coating process that includes a fluidized bed coating machine or other coating equipment and methods. The process for coating the granulated materials with a sufficient amount of coating agent is used in order to achieve timed release or enteric protection through gut transit through the stomach and into the small intestine for release and absorption.

Other excipients may also include starch, maltodextrin, and polyethylene glycol ("PEG", which most preferably has an average molecular weight of approximately 3350). Although the weight percentages of the various constituents may vary, preferably, each excipient constitutes from 1-10% by weight, more preferably 2-6% by weight, and most preferably approximately 4-5% by weight of the final coated product. In one embodiment, the weight percent of the methacrylate copolymers constitutes 1-10%, more preferably 2-6% and most preferably 4-5%. Certain bioactive compounds can also be included in low percentage ranges (e.g., from 0.01%-2.5% by weight of the final product) that can synergistically increase the effects of creatine and amino acids, and include: sugar polymers, and polyphenolic compounds with active and functional characteristics.

The particles are coated in a percentage of coating excipients so that the active ingredients range from at least 45-50% up to a maximum of 90% of the final product mass. Preferred coating agents include natural methacrylate copolymers (e.g., poly (ethylacrylate-co-methyl methacrylate CAS No. 9010-88-2), anionic methacrylate copolymer (e.g., poly (methyl acrylate-co-methylmethacrylate-comethacrylic acid CAS No. 26936-24-3), and/or basic methacrylate copolymer (e.g., poly (butyl methacrylate-co-(2-dimethylaminoethyl) methacrylatecomethyl methacrylate, CAS No. 24938-16-17). The particular coating agent selected is that which preferably results in a minimal degradation of active ingredients in the acid environment of the stomach (most preferably less than 15% loss) and release of active ingredients in the alimentary canal subsequent to the stomach over a 3-6 hour time frame.

In one embodiment of the present invention, the constituents prior to coating include disodium-phosphocreatine plus γ-cyclodextrin. These constituents are preferably co-granulated prior to coating with methacrylate copolymers. The coating preferably constitutes from 1% to 5% (w/w) of the final product. The cyclodextrin component may also be a mixture selected from the group consisting of α, β and γ-cyclodextrins.

In another embodiment of the present invention, the granulated constituents to be coated include a phosphocreatine in a form not a sodium salt, trisodium citrate, and a mixture selected from the group consisting of α, β and γcyclodextrins. These constituents are preferably co-granulated prior to coating with methacrylate copolymers constituting from 1% to 5% (w/w) of the final product.

In yet another embodiment of the present invention, the constituents prior to coating include one or more forms of creatine selected from the group consisting of phosphocreatine, creatine HCl and creatine monohydrate plus cyclodextrin selected from the group consisting of α-, β- and γ-cyclodextrins. To the extent that sodium ions are not present in some or all of the creatine to be co-granulated, additional sodium, most preferably in the form of trisodium citrate is supplied to the formulation, preferably so as to result in a molecular ratio of from about 1-3 sodium: creatine. Optionally, one or more phenolic compounds are also included. These constituents are preferably co-granulated prior to coating with methacrylate copolymers.

It is further contemplated that the creatine formulations of the present invention may be useful for minimizing symptoms of Parkinson's disease and of muscle-wasting diseases. Higher dosages, for example, from 2 to 20 grams per day, are recommended to minimize symptoms of Parkinson's disease and muscle wasting diseases and conditions.

DESCRIPTIONS OF THE FIGURES

DETAILED DESCRIPTION OF PREFERRED EMBODIMENTS

Figure 1:
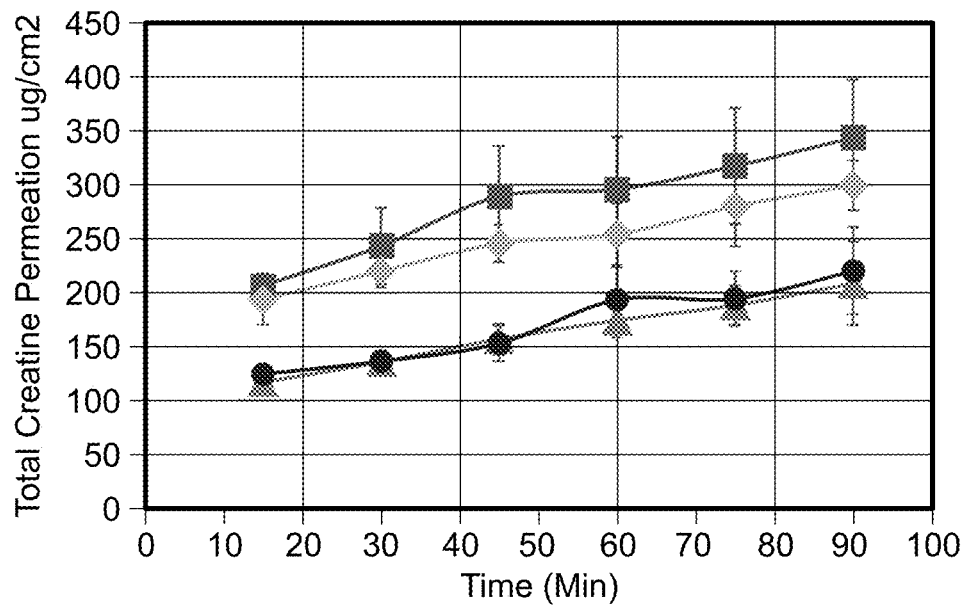
FIG. 1 illustrates creatine permeation through a Caco-2 monolayer in simulated gastric and intestinal buffers, of formulations of creatine HCl with and without cyclodextrin compared to formulations containing disodium phosphocreatine with and without cyclodextrin.

In looking for a formulation manifesting improved creatine uptake in the digestive tract, a CaCo2 cellular diffusion model substantially similar to that described by A. K. Dash, et al., "Evaluation of Creatine Transport Using Caco-2 Monolayers as an In Vitro Model for Intestinal Absorption" was used. Uptake of creatine HCl ("CrHCl") was compared to that of disodium phosphocreatine with and without cyclodextrin.

The various compounds used in the experiments supporting the present invention include disodium creatine phosphate from Tiancheng International Inc., creatine HCl from Tiancheng International Inc., trisodium citrate from Cargill, creatine monohydrate from Sigma Life Science, C3630, creatinine from Sigma Aldrich, C4255, Water-Optima from Fisher Scientific, W 7-4, acetonitrile—Optima from Fisher Scientific, A995-4, Eudraguard® control from Evonik, Eudraguard® protect readymix from Evonik, ammonium sulfate, ACS from RICCA, RDCA0520-500B1, DMEM from Corning cellgro, 50-013-PC, Hanks' balanced salts (modified) from Sigma, H2387, and monobasic potassium phosphate from Spectrum, P0200.

To evaluate creatinine formation in simulated gastric and simulated intestinal buffers, a solution of 0.2N was prepared by dilution of 1 g NaOH QS to 125 mL with DI water. Simulated intestinal fluid without enzymes was prepared with 6.8 g monobasic potassium phosphate, 77 mL 0.2 N sodium hydroxide, pH adjusted to 6.8±0.1 using NaOH or HCl, with dissolution and QS to 1 L with DI water, to a final pH should of 6.8±0.1. To prepare simulated gastric fluid without enzymes, 2.0 g sodium chloride was mixed with 7.0 mL concentrated HCl, then dissolved and diluted to 1 L with DI water, with the resulting pH at approximately 1.2. Prior to experimentation, these simulated fluids were filtered at 0.2 um.

After fluid preparation, 159 mg of disodium phosphocreatine were placed into each of two 250 mL volumetric flasks. The simulated gastric fluid described above was added to one of the flasks to 250 mL and the simulated intestinal fluid was added to the other of the flasks to 250 mL. 93 mg of creatine hydrochloride were placed into each of the two other volumetric flasks. The simulated gastric fluid described above was added to one of the flasks to 250 mL and the simulated intestinal fluid was added to the other flasks to 250 mL.

At test time 0 (start), a 1 mL sample was withdrawn from each volumetric flask, filtered at 0.2 um and injected and measured by high-performance liquid chromatography (UPLC) immediately. Six separate withdrawals of 20 mL of each of the samples were then placed in scintillation vials for a total of 24 vials. Three samples from each set were incubated in an orbital shaker at 100 rpm and 37 C. Three other samples from each set were retained at room temperature on an orbital shaker at 100 rpm. 1 ml samples were then drawn from all vials at 0.5, 1, 2, 4, 6, 12, 24 and 48 hours, filtered at 0.2 um and injected into the UPLC immediately. Retained filtered samples were saved refrigerated at 4 C until after the completion of the study. A creatinine internal standard of 2.5 mM, 71 mg/250 ml, 0.2 um filtered in either simulated gastric or intestinal fluid was spiked into the retained samples at 50 ul creatinine to 450 ul sample and rerun on the UPLC to ensure proper detection of creatinine formation.

Thereafter, for all samples from each formulation were monitored apical to basolateral (A-B) for 90 minutes in 15 minute increments through a Caco 2-membrane registering an average TEER of 2500 Ohm*cm2. Samples were monitored for creatine and creatinine content. No significant quantities of creatinine were detected. Creatine permeation through the Caco-2 monolayer is illustrated in FIG. 1, with data as summarized below in Table I.

TABLE I

|  | 15 min | 30 min | 45 min | 60 min | 75 min | 90 min |
|---|---|---|---|---|---|---|
| ◆ Disodium phosphocreatine | 194.3 | 220.1 | 245.8 | 254.3 | 280.3 | 299.7 |
| ■ Disodium phosphocreatine w/cyclodextrin | 206.8 | 243.4 | 289.4 | 295.7 | 317.5 | 343.9 |
| ▲ Creatine hydrochloride | 124.8 | 136.7 | 153.3 | 193.6 | 194.6 | 220.3 |
| ● Creatine hydrochloride w/cyclodextrin | 117.2 | 136.0 | 157.1 | 174.6 | 188.7 | 208.5 |

Creatine permeation was measured in micrograms per square centimeter ($\mu/cm^2$) for each formulation at 30, 45, 60, 75 and 90 minutes after test start. As is readily apparent, the disodium phosphocreatine formulations had substantially greater creatine permeation at all times throughout the test, as compared to creatine permeation from the creatine HCl formulations. This result was unexpected. Indeed, at test end, creatine permeation of the disodium phosphocreatine formulation in which cyclodextrin was not premixed, was measured at 299.7$\mu/cm^2$, which is 136% of the creatine permeation of the creatine HCl formation measured at 220.3$\mu/cm^2$.

The formulations of creatine HCl without the presence of cyclodextrin showed little difference in creatine permeation throughout the 90 minute test period as compared to the formulations of creatine HCl premixed with cyclodextrin. In contrast, the formulations of disodium phosphocreatine exhibited consistently increased creatine permeation, which ranged from 6.4% at 15 minutes after test start (206.8$\mu/cm^2$ as compared to 194.3$\mu/cm^2$) to 15% at 90 minutes after test start (343.9$\mu/cm^2$ as compared to 299.7$\mu/cm^2$) when premixed with the cyclodextrin, as compared to disodium phosphocreatine permeation when no cyclodextrin was present. This result of the presence of the cyclodextrin was completely unexpected.

Further studies were then undertaken to confirm above results comparing creatine dissolution of coated and uncoated disodium phosphocreatine granules in simulated gastric and intestinal buffers (without enzymes). Once again, the CaCo2 cellular diffusion model substantially similar to that described by A. K. Dash, et al., "Evaluation of Creatine Transport Using Caco-2 Monolayers as an In Vitro Model for Intestinal Absorption" was used. More particularly, two formulations were studied, one coated with Eudraguard® control applied in a fluidized bed coater.

EUDRAGUARD® control, a product of Evonik Nutrition & Care GmbHis, is a functional coating designed for enteric release, sustained-release formulations and gastro retention. The product is specifically designed for dietary supplement applications that require reliable and reproducible controlled-release profiles. EUDRAGUARD® control meets the regulatory requirements for use in dietary supplements in the European Union (E 1206) and the United States (GRAS).

EUDRAGUARD® protect, also a product of Evonik Nutrition & Care GmbHis, a polymer designed for immediate release formulations. It offers reliable taste and odor masking and protects ingredients from light, moisture and oxygen, which could impact ingredient effectiveness. The coatings give a smooth and even finish. EUDRAGUARD® protect ReadyMix is a ready-to-use powder that contains all the ingredients needed to form effective protective coatings for nutraceuticals. The spray suspension is formed by adding water to the ReadyMix while stirring. EUDRAGUARD® protect ReadyMix, a one-component system, is a ready-to-use mixture of the polymer plus excipients that can be augmented. It can be applied to solid oral dosage forms such as tablets, capsules and multiparticules. And because it is based on EUDRAGUARD® protect, the mix meets the regulatory requirements for use in dietary supplements in the European Union (E 1205) and the United States (GRAS).

For all samples 10 Mm creatine was present in the initial solution. Samples from each formulation were monitored apical to basolateral (A-B) for 90 minutes in 15 minute increments through a Caco 2-membrane registering an average TEER of 2500 Ohm*$cm^2$. Samples were monitored for creatine and creatinine content. No significant quantities of creatinine were detected for the duration of the study.

Figure 2:
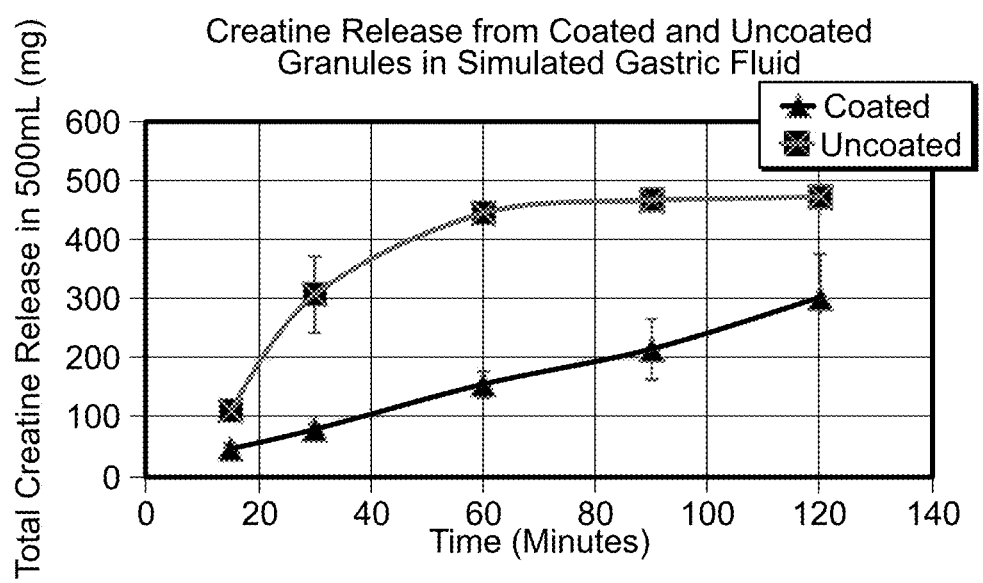
FIG. 2 illustrates creatine release from coated and uncoated granules in simulated gastric fluid over time.
Figure 3:
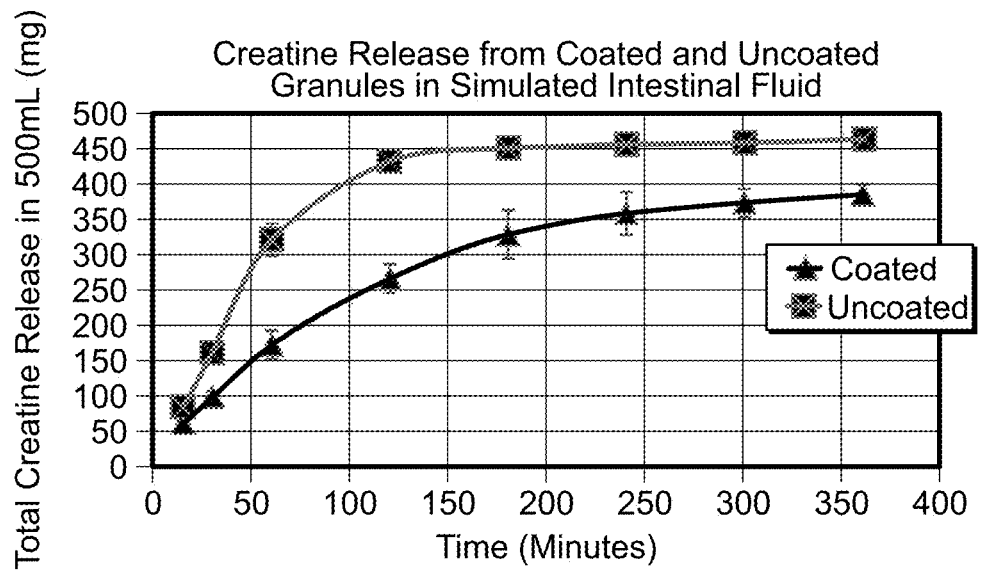
FIG. 3 illustrates creatine release from coated and uncoated granules in simulated intestinal fluid over time.
Figure 4:
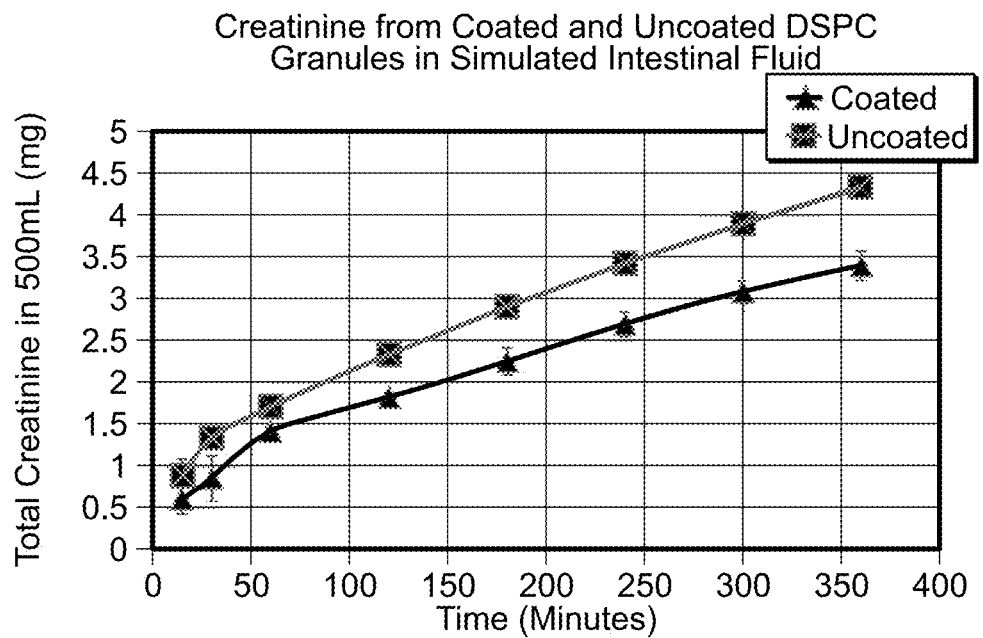
FIG. 4 illustrates creatinine levels from coated and uncoated disodium phosphocreatine (DSPC) in simulated intestinal fluid overtime.
Figure 5:
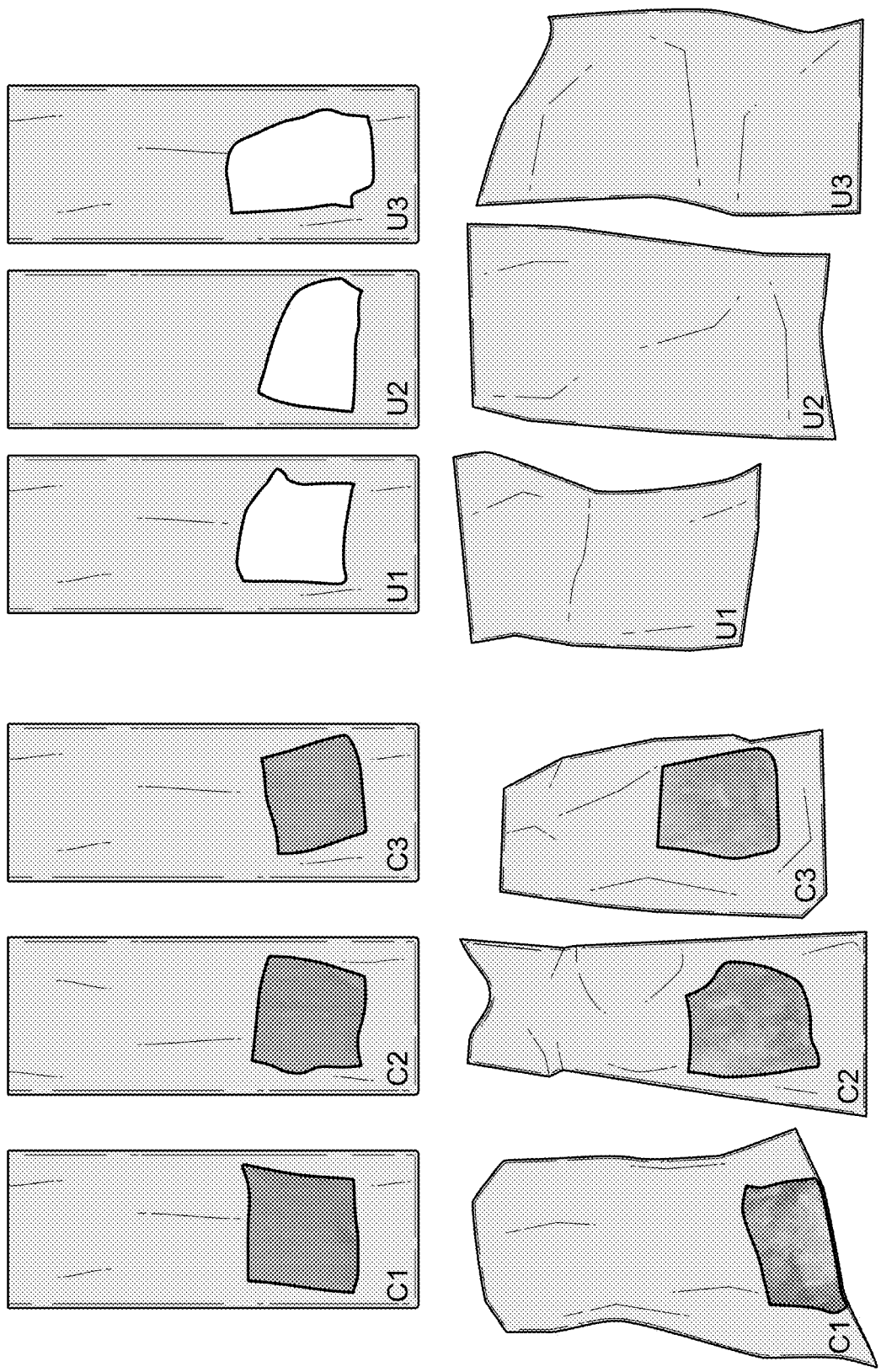
FIG. 5 illustrates coated (blue) and uncoated (white) granules in sealed teabags before (upper) and after (lower) gastric buffer.

Creatine permeation through the Caco-2 monolayer is illustrated in FIGS. 2, 3 and 4, below with data as summarized below, respectively, in Tables II, III and IV which follow:

TABLE II

|  | 15 min | 30 min | 60 min | 90 min | 120 min |
|---|---|---|---|---|---|
| Disodium phosphocreatine coated | 47.4 | 80.4 | 156.7 | 216.1 | 302.7 |
| Disodium phosphocreatine w/cyclodextrin uncoated | 111.8 | 307.9 | 444.6 | 466.4 | 471.4 |

TABLE III

|  | 30 min | 60 min | 120 min | 180 min | 240 min | 300 min | 360 min |
|---|---|---|---|---|---|---|---|
| Disodium phosphocreatine coated | 161.81 | 172.1 | 266.1 | 328.3 | 358.0 | 373.0 | 384.6 |
| Disodium phosphorcreatine uncoated | 84.4 | 321.1 | 431.3 | 449.4 | 455.1 | 457.1 | 462.2 |

These data follow with the loss of matter observed from the samples (samples retained). It was observed that in simulated gastric buffer there was only one sample/time point that showed significant creatinine formation. The amount at that time point calculated to a total of 15 mg/500 ml creatinine formation in 2 hours. There was no formation of creatinine observed in the coated gastric samples. Measurements were made, with the following results:

TABLE IV

|  | 15 min | 60 min | 120 min | 180 min | 240 min | 300 min | 360 min |
|---|---|---|---|---|---|---|---|
| Disodium phosphocreatine coated | 0.86 | 1.42 | 1.83 | 2.24 | 3.70 | 3.08 | 3.39 |
| Disodium phosphocreatine uncoated | 0.87 | 1.71 | 2.33 | 2.89 | 3.42 | 3.89 | 4.32 |

Dissolution studies were also undertaken in which granules were prepared containing 85.73% (w/w) disodium phosphocreatine, 4.5% (w/w) Eudraguard® protect, and 4.75% (w/w) PEG 3350. In other embodiments other polyethylene glycols may be used. Uncoated granules contained 5% (w/w) lactose, coated granules contained 5% (w/w) Eudraguard® control. Wet granulation of particles was performed using a 10% solution of PEG 3350 in ethanol slowly added while powders were mixed using a high sheer mixer. Wet granules were sieved through 30 and 60 mesh sieves. Granules were then dried and granules between 100 and 140 mesh by sieve were collected to produce granules between 100 and 150 μm. For purposes of experimentation, blue dye was added to the Eudraguard® control <0.1% w/w, and particles were coated using the following parameters:

| Parameters | Values |
|---|---|
| Atomization Rate | 1.5 Barr |
| Air flow rate | 52 m$^3$/hr |
| Inlet Temperature | 80° C. |
| Drying Chamber Temperature | 50° C. |
| Filter Cleaner knob | 2 |
| Spray Rate | Dial reading 5 (1 ml/min) |

Coated granules were sieved and granules in the size range 150-250 μm (between 60 and 100 mesh) were collected for dissolution studies. Dissolution of coated and uncoated granules sized 150-250 μm was performed by weighing approximately 470 mg of granules into weighed tea bags and heat sealed. The dissolution protocol was as follows:
  1) Apparatus: USP type II Basket Apparatus
  2) Temperature: 370±0.5° C.
  3) Volume of the dissolution media: 500 mL
  4) Dissolution Media:
    USP Simulated Gastric Buffer pH 1.2
    USP Simulated Intestinal Fluid pH 6.8
  5) Sampling Points:
    Gastric exposure: 15, 30, 60, 90, 120 min
    Intestinal exposure: 15, 30, 60, 120, 180, 240, 300, 360 min
  6) Sample Volume: one mL
  7) Samples withdrawn were replaced by addition of equal volume of fresh dissolution medium, removed sample amounts were accounted for in the calculations.
  8) Samples were filtered and analyzed by HPLC to determine the concentration of Creatine and Creatinine In one experiment, coated and uncoated granules were placed in sealed teabags. The Eudraguard® control <0.1% w/w prior to coating, resulted in teabags with blue contents, as compared to teabags with uncoated white granules. The top row above shows 3 teabags containing blue coated granules on the left and 3 teabags with uncoated white granules on the right. The lower row illustrates the teabags after placement in the gastric buffers. The 3 teabags on the left contain intact granules, as evidenced by blue coating. The 3 teabags on the right are mostly empty, the granules having dissolved in the gastric buffer.

Preferred ranges of the compositions of the present invention contain 75% to 95% (w/w) disodium phosphocreatine, 0 to 10% cyclodextrins as a mixture selected from the group consisting of α, β and γ-cyclodextrins, 0 to 10% (w/w) Eudraguard® protect, and 0 to 10% (w/w) PEG 3350. Coated granules preferably contain 1% to 10% (w/w) Eudraguard® control. Preferable use of these compositions are as oral supplementation for mammals. They are preferably dosed in powder, tablet, and beverage forms.

Preferred methods of manufacturing a creatine supplement of the present invention include co-granulating one or more creatine compounds, cyclodextrin, and a sodium source to form a granular composition having an average particle size of from 150 to 850 microns; and then coating the granular composition with methacrylate copolymers to produce a coated creatine supplement. The one or more creatine compounds can include phosphocreatine and the sodium source can include trisodium citrate. Also, the one or more creatine compounds may include disodium phosphocreatine and the disodium moiety of the phosphocreatine may constitute all or part of the sodium source. Also, the creatine compound may be selected from the group consisting of creatine monohydrate, creatine HCl and phosphocreatine, and sodium of the sodium source may be present in a molar ratio of sodium to creatine of from 1:1 to 3:1. In the present invention, the coating step may comprise spray drying the granular compound utilizing a fluidized bed technique. The resulting coated creatine supplement resulting from the methodologies described herein is included with the scope in the present invention.

An oral creatine supplement of the present invention most preferably comprises disodium phosphocreatine and cyclodextrin selected from the group consisting of alpha, beta and gamma cyclodextrins. This oral supplement is preferably in the form of a powder, an encapsulated product, a tablet or beverage. Preferably, the creatine supplement is coated, most preferably with a methacrylate copolymer.

In other embodiments, an oral creatine supplement of the present invention comprises disodium phosphocreatine, polyethylene glycol and cyclodextrin selected from the group consisting of alpha, beta and gamma cyclodextrins. Such supplements are preferably coated with a coating comprising a methacrylate copolymer, most preferably, Eudraguard® protect as the methacrylate copolymer coating. Preferably, the creatine supplement comprises 85% disodium phosphocreatine, 5% polyethylene glycol, 5% cyclodextrins and is coated with a 5% by weight of the formulation coating comprising methacrylate copolymer. Other embodiments of the oral creatine supplement formulation composition comprise 75% to 95% (w/w) disodium phosphocreatine, 0 to 10% (w/w) cyclodextrins as a mixture selected from the group consisting of α, β and γ-cyclodextrins, 0 to 10% (w/w) Eudraguard® protect methacrylate copolymer, and 0 to 10% (w/w) PEG 3350. Also preferred are embodiments of the oral creatine supplement formulation composition which comprise 75% to 95% (w/w) disodium phosphocreatine, 2% to 10% (w/w) cyclodextrins selected from the group consisting of a, p and γ-cyclodextrins, and 2% to 10% (w/w) Eudraguard®.

In other embodiments of the oral creatine supplement of the present invention, the formulations include coated granules preferably containing 1% to 10% (w/w) utilizing Eudraguard® control as the methacrylate copolymer.

Each of the oral creatine supplements of the present invention are preferably used as a supplement for mammals, most preferably dosed as a powder, tablet, capsule or as beverage forms. They can be used to treat a muscle wasting disorder such as cachexia, sarcopenia or the like. These products can also be used to enhance body muscle mass for sports performance applications, sports injury recovery or for maintenance of normal muscle tone during the aging process of a mammal.

The invention claimed is:

1. A coated creatine supplement manufactured by a process comprising the steps of:
co-granulating disodium phosphocreatine, and gamma cyclodextrin; to form a granular composition having an average particle size of from 150 to 850 microns; and
coating the granular composition with methacrylate copolymers to produce the coated creatine supplement;
wherein the coated creatine supplement comprises:
75% to 95% by weight disodium phosphocreatine;
2% to 10% by weight gamma cyclodextrin; and
1-10% by weight methacrylate copolymer coating.

2. An oral creatine supplement comprising:
at least 75% by weight disodium phosphocreatine; and
at least 2% by weight of gamma cyclodextrin;
wherein the oral creatine supplement exhibits improved creatine permeation and bioavailability.

3. The oral creatine supplement of claim 2, where the oral creatine supplement is in the form of a powder, an encapsulated product, a tablet or beverage.

4. The oral creatine supplement of claim 2, further comprising a coating.

5. The oral creatine supplement of claim 4, wherein the coating comprises a methacrylate copolymer.

6. An oral creatine supplement comprising:
at least 75% by weight disodium phosphocreatine;
at least 2% by weight polyethylene glycol; and
at least 2% by weight gamma cyclodextrins;
wherein the oral creatine supplement exhibits improved creatine permeation and bioavailability.

7. The oral creatine supplement of claim 6, wherein the oral creatine supplement further comprises a methacrylate copolymer coating.

8. The oral creatine supplement of claim 7, wherein the coating is poly (butyl methacrylate-co-(2-dimethylaminoethyl) methacrylate-comethyl meth-acrylate) or poly (ethylacrylate-co-methyl methacrylate) as the methacrylate copolymer coating.

9. The oral creatine supplement of claim 4, wherein the oral creatine supplement comprises, by weight, 85% disodium phosphocreatine, 5% gamma cyclodextrins and 2-5% methacrylate copolymer coating.

10. An oral creatine supplement comprising:
75% to 95% by weight disodium phosphocreatine,
2% to 10% by weight gamma cyclodextrins,
1% to 10% by weight Poly (butyl methacrylate-co-(2-dimethylaminoethyl) methacrylate-comethyl methacrylate) coating.

11. An oral creatine supplement comprising:
75% to 95% by weight disodium phosphocreatine;
2% to 10% by weight gamma cyclodextrin; and
1% to 10% by weight of methacrylate copolymer coating.

12. An oral creatine supplement comprising:
75% to 95% by weight disodium phosphocreatine;
2% to 10% by weight gamma cyclodextrin; and
1% to 10% by weight poly (ethylacrylate-co-methyl methacrylate) coating.

13. The oral creatine supplement of claim 11, wherein the oral creatine supplement is in a form selected from the group consisting of a powder, tablet, capsule or beverage.

14. The oral creatine supplement of claim 2 for treating a muscle wasting disorder.

15. The oral creatine supplement of claim 2 to enhance body muscle mass for sports performance applications, sports injury recovery or for maintenance of normal muscle tone during the aging process of a mammal.

16. The oral creatine supplement of claim 7, comprising:
at least 85% by weight disodium phosphocreatine;
2-10% by weight gamma cyclodextrins;
2-10% by weight polyethylene glycol, and
1-10% by weight methacrylate copolymer coating.

17. The oral creatine supplement of claim 2, further comprising alpha or beta cyclodextrins.

18. The oral creatine supplement of claim 5, wherein the creatine supplement is coated with poly (butyl methacrylate-co-(2-dimethylaminoethyl) methacrylate-comethyl meth-acrylate) or poly (ethylacrylate-co-methyl methacrylate) as a methacrylate copolymer.

19. An oral creatine supplement of claim 5, wherein the coating is a mixture of Poly (butyl methacrylate-co-(2-dimethylaminoethyl) methacrylate-comethyl meth-acrylate) and poly (ethylacrylate-co-methyl methacrylate).

20. An oral creatine supplement of claim 11, wherein the coating is a mixture of Poly (butyl methacrylate-co-(2-dimethylaminoethyl) methacrylate-comethyl meth-acrylate) and poly (ethylacrylate-co-methyl methacrylate).

* * * * *